US005549654A

United States Patent [19]
Powell

[11] Patent Number: 5,549,654
[45] Date of Patent: Aug. 27, 1996

[54] INTERACTIVE INTERPRETATION OF EVENT MARKERS IN BODY-IMPLANTABLE MEDICAL DEVICE

[75] Inventor: Richard M. Powell, Bloomington, Minn.

[73] Assignee: Medtronic, Inc., Minneapolis, Minn.

[21] Appl. No.: 228,237

[22] Filed: Apr. 15, 1994

[51] Int. Cl.$^6$ .................................................. A61N 1/37
[52] U.S. Cl. ............................................................ 607/32
[58] Field of Search ........................... 607/25, 26, 30–32, 607/60; 128/696, 702–705, 710–712; 364/413, 6

[56] References Cited

U.S. PATENT DOCUMENTS

| | | | |
|---|---|---|---|
| 4,809,697 | 3/1989 | Causey, III et al. | 607/30 X |
| 4,989,610 | 2/1991 | Patton et al. | 128/712 X |
| 5,224,486 | 6/1993 | Lerman et al. | 628/710 X |
| 5,345,362 | 9/1994 | Winkler | 361/681 |
| 5,372,607 | 12/1994 | Stone et al. | 607/30 |

*Primary Examiner*—William E. Kamm
*Assistant Examiner*—Jeffrey R. Jastrzab

*Attorney, Agent, or Firm*—Reed A. Duthler; Harold R. Patton

[57] ABSTRACT

An automatic implantable device system including an implantable device which communicates with an external programming unit via uplink and downlink telemetry. The implanted device is capable of transmitting event markers to the external device, the event markers reflecting the occurrence of identified physiologic and device-initiated events. The external device includes circuitry for generating an interactive diagram illustrating the interrelation between marker events, and a display screen for presenting a graphical image of the marker diagram to the user. In addition, the external device defines a plurality of "hot spots" in the area of the diagram, such that when a user selects a particular area of the diagram on the display, using, for example, a mouse or other cursor control device, a context-sensitive explanatory message is displayed to the user. In the disclosed embodiment, expert system software is executed by a computer subsystem of the external device. The expert system software is supplied with a knowledge base specific to a particular model of implanted device, the knowledge base providing the expert system with the rules necessary for proper interpretation and explanation of the event marker diagram.

10 Claims, 7 Drawing Sheets

INTERACTIVE INTERPRETATION OF EVENT MARKERS IN BODY-IMPLANTABLE MEDICAL DEVICE

FIELD OF THE INVENTION

This invention relates to the field of automatic, body-implantable medical device systems, and more particularly relates to systems having the capacity for displaying event and timing data associated with operation of an implanted medical device.

BACKGROUND OF THE INVENTION

A wide variety of automatic, body-implantable medical devices for performing various therapeutic and diagnostic functions are known in the prior art. A common example, the implantable cardiac pacemaker, functions to deliver electrical stimulating pulses to a patient's heart. Early pacemakers, which typically included discrete analog components, delivered stimulating pulses at a fixed periodic rate without regard to the presence or absence of naturally occurring heartbeats. Later, so-called demand pacemakers, which were capable of sensing intrinsic cardiac activity and delivering stimulating pulses only when necessary, were developed. Modern pacemakers typically utilize digital circuitry of considerable complexity, and are thus vastly more sophisticated in their operational capabilities. The increased capabilities of state-of-the-art pacemakers has expanded the operating modalities to encompass both chambers of the heart, and has also led to the addition of features such as multiprogrammability.

As the functional sophistication and complexity of implantable devices such as pacemakers, defibrillators, cardioverters and the like has increased over the years, it has been increasingly more important for such devices to be equipped with a telemetry system for facilitating communication of information between the implanted device and an external programming and/or control unit.

For example, even in connection with the earliest fixed-rate, non-inhibited pacemakers, it was apparent that it would be desirable for a physician to noninvasively exercise at least some amount of control over the device, e.g., to turn the device on or off, or to adjust the fixed pacing rate, after implant. In early devices, one way the physician was able to have some control over implantable device operation was through the provision of a magnetic reed switch in the implantable device. After implant, the reed switch would be actuated (closed) by placing a magnet over the implant site. Reed switch closure could then be used, for example, to alternately activate and deactivate the device. Alternatively, the fixed pacing rate of the device could be adjusted up or down by incremental amounts based upon the duration of the reed switch closure interval. Many different schemes utilizing a reed switch to adjust operational parameters of medical devices have been developed. See, for example, U.S. Pat. No. 3,311,111 to Bowers; U.S. Pat. No. 3,518,997 to Sessions; U.S. Pat. No. 3,768,486 to Berkovits; U.S. Pat. No. 3,631,860 to Lopin; U.S. Pat. No. 3,738,369 to Adams et al., U.S. Pat. No. 3,805,796 to Terry, Jr.; and U.S. Pat. No. 4,066,086 to Alferness et al.

The need to communicate more and more information to implanted devices with increasing levels of functionality quickly rendered the simple reed switch closure arrangement insufficient. Also, it has become apparent that it is desirable not only to allow information to be communicated to the implanted device from an external unit (referred to as "downlink telemetry"), but also to enable the implanted device to communicate information to the external unit (referred to as "uplink telemetry").

Uplink telemetry capabilities in an implantable device system are particularly advantageous with state-of-the-art pacemakers which interact with the heart in a complex fashion. Even relatively simple diagnostic tasks, such as verifying proper operation of the pacemaker, can be difficult with sophisticated, state-of-the art pacemakers, whose pacing algorithms involve, for example, automatically varying timed responses to sensed inputs. In addition, a pacemaker's pacing algorithm may be such that the pacemaker's responses may depend upon prior events, which means that interpretation of responses also requires information about what events have been sensed by the device and how such events are interpreted by the device.

Traditionally, verification of pacemaker operation was less difficult, and was accomplished with the aid of an electrocardiogram (ECG), which shows electrical cardiac activity detected either on the skin surface of the patient (surface ECG), or from an implanted sensing lead (intracardiac ECG). As will be appreciated by those of ordinary skill in the art, the ECG displays the physiological waveform of the heart as a complex periodic waveform with P, Q, R, S, and T portions. Pacemaker stimulating pulses appear as narrow pacemaker artifacts on an ECG trace. By noting the relationship between the pacemaker artifacts and various elements of the physiological waveform, the physician can analyze the operating characteristics of the pacemaker to verify its proper and safe performance.

Those of ordinary skill in the art will further appreciate, however, that modern dual-chamber pacemakers, with complex pacing algorithms and features such as rate- or activity-responsiveness, multiple chamber sensing and pacing, multiprogrammability, multi-modal operation, and the like, have responses to physiological events which may be difficult to analyze based solely upon the observations of a patient's electrocardiogram. Consequently, there has been a need to provide additional uplink telemetry information to the attending physician or clinician to simplify the analysis of pacemaker operation.

One prior art technique which is directed to the above-described problem is presented in U.S. Pat. No. 3,662,759 to Dabolt. According to the Dabolt '759 patent, a narrow sub-threshold pulse is applied to the heart via the pacing lead system each time the demand pacemaker escape interval is reset by sensed spontaneous cardiac activity. This sub-threshold pulse is insufficient to stimulate the heart, but its steep rise time generates sufficient radio-frequency harmonics to be detected by a conventional radio receiver. In operation, a radio "click" is produced each time a naturally occurring R-wave is detected and used by the pacemaker circuitry to reset the escape interval of the pacemaker. Thus, according to the Dabolt '759 patent, proper sensing by the pacemaker's sensing circuitry can be verified. Although the system disclosed in the Dabolt '759 patent provides a convenient method of producing a remote indication of a sensed event with a minimum of equipment, no permanent record of the sensed event is produced by this technique, nor is the system applicable to the analysis of operation of more complex pacemakers. In addition, the delivery of sub-threshold pulses in accordance with the Dabolt '759 patent may result in earlier depletion of the implanted device's power supply.

Prior art uplink telemetry systems are known in which sensed diagnostic data or patient data is transmitted, via an uplink telemetry channel, to an external apparatus for display. For example, it is known to provide a pacemaker with a separate analog uplink telemetry channel for transmission of real-time intracardiac ECG data, the analog transmission channel being separate from and in addition to the downlink channel for operator programming and interrogation. While, of course, multiple channels can be used if there is no limit on expense, size, or power requirements, there is a great need for efficient use of the available communications channel, in order to handle the normal programming and interrogation requirements, as well as the transmission of patient and other diagnostic data.

Known pacemaker systems have accordingly been provided with what is referred to as Marker Channel™ functionality, in which uplink information regarding the pacemaker's operation and the occurrence of physiological events is communicated to an external unit. The Marker Channel™ information can then be printed or displayed in relation to an ECG so as to provide supplemental information regarding pacemaker operation. For example, events such as pacing or sensing of natural heartbeats are recorded with a mark indicating the time of the event relative to the ECG. This is helpful to the physician in interpreting the ECG, and in verifying proper operation of the pacemaker. One example of a Marker Channel™ system is disclosed in U.S. Pat. No. 4,374,382 to Markowitz, entitled "Marker Channel Telemetry System for a Medical Device." The Markowitz '382 patent is hereby incorporated by reference herein in its entirety.

Existing systems which provide a Marker Channel™ output operate basically by outputting an indication of a physiological or pacemaker event, e.g., a delivered stimulating pulse or a sensed heartbeat, at about the time of the event, thereby inherently providing the timing of the event in relation to the recorded ECG. Alternatively, the Marker Channel™ system can accumulate data over a period of time, e.g., one cardiac cycle, and transmit a batch of data for that interval at the beginning of the next interval. This is what appears to be proposed in U.S. Pat. No. 4,601,291 to Boute et al., entitled "Biomedical System with Improved Marker Channel Means and Method." The Boute et al. '291 patent is also incorporated by reference herein in its entirety.

Various telemetry systems for providing the necessary communications channels between an external unit and an implanted device have been shown in the art. Telemetry systems are disclosed, for example, in the following U.S. Pat. Nos.: U.S. Pat. No. 4,539,992 to Calfee et al. entitled "Method and Apparatus for Communicating With Implanted Body Function Stimulator"; U.S. Pat. No. 4,550,732 to Batty Jr. et al. entitled "System and Process for Enabling a Predefined Function Within An Implanted Device"; U.S. Pat. No. 4,571,589 to Slocum et al. entitled "Biomedical Implant With High Speed, Low Power Two-Way Telemetry"; U.S. Pat. No. 4,676,248 to Berntson entitled "Circuit for Controlling a Receiver in an Implanted Device"; U.S. Pat. No. 5,127,404 to Wyborny et al. entitled "Telemetry Format for Implanted Medical Device"; U.S. Pat. No. 4,211,235 to Keller, Jr. et al. entitled "Programmer for Implanted Device"; and U.S. Pat. No. 4,556,063 to Thompson et al. entitled "Telemetry System for a Medical Device". The Wyborny '404 and Thompson et al. '063 patents are hereby incorporated by reference herein in their respective entireties.

Typically, telemetry systems such as those described in the above-referenced patents are employed in conjunction with an external programming/processing unit. One programmer for non-invasively programming a cardiac pacemaker is described in its various aspects in the following U.S. Patents to Hartlaub et al., each commonly assigned to the assignee of the present invention and each incorporated by reference herein in its entirety: U.S. Pat. No. 4,250,884 entitled "Apparatus For and Method Of Programming the Minimum Energy Threshold for Pacing Pulses to be Applied to a Patient's Heart"; U.S. Pat. No. 4,273,132 entitled "Digital Cardiac Pacemaker with Threshold Margin Check"; U.S. Pat. No. 4,273,133 entitled "Programmable Digital Cardiac Pacemaker with Means to Override Effects of Reed Switch Closure"; U.S. Patent No. 4,233,985 entitled "Multi-Mode Programmable Digital Cardiac Pacemaker"; and U.S. Pat. No. 4,253,466 entitled "Temporary and Permanent Programmable Digital Cardiac Pacemaker".

Aspects of the programmer that is the subject of the foregoing Hartlaub et al. patents (hereinafter "the Hartlaub programmer") are also described in U.S. Pat. No. 4,208,008 to Smith, entitled "Pacing Generator Programming Apparatus Including Error Detection Means" and in U.S. Pat. No. 4,236,524 to Powell et al., entitled "Program Testing Apparatus". The Smith '008 and Powell et al. '524 patents are also incorporated by reference herein in their entirety.

A commercially available example of a programmer used for communicating with implanted medical devices is the Model 9760, manufactured by Medtronic, Inc., Minneapolis, Minn. The Model 9760 programmer is based on an general-purpose microprocessor platform, e.g., on an Intel 80X86 microprocessor or the like, and includes a text and graphics display screen similar to that conventionally used with personal computers. The graphics display screen allows graphical depictions, for example, of real-time ECG waveforms transmitted from the implanted device, to be presented to the physician or clinician. Additionally, for pacemakers which have a Marker Channel™ capability, the event markers associated with various physiologic and pacing events detected by the implanted device can be superimposed upon or displayed alongside the ECG signal on the programmer's display, allowing the physician or clinician to observe the time relation between marker events and the ECG waveform. This gives the physician or clinician some degree of insight into whether the pacemaker is operating properly. However, as noted above, interpreting and understanding the Marker Channel™ data, even when superimposed upon an ECG waveform, can be difficult in view of the complex responses exhibited by state-of-the-art pacemakers.

The difficulties associated with interpreting, understanding, and or verifying proper implanted device response are exacerbated when the device is operable in multiple modes, e.g., when there is defined for the device a pacing algorithm for treating bradycardia (generally the function of a pacemaker), but also cardioversion and defibrillation algorithms for the treatment of tachycardia and fibrillation. In known pacemaker/cardioverter/defibrillators (PCDs), both ventricular fibrillation and ventricular tachycardia are identified and treated in addition to the identification and treatment of bradycardia. In PCDs, ventricular fibrillation and ventricular tachycardia are typically identified using complex rate-based criteria. In such devices, their operational algorithms commonly specify rate or interval ranges that characterize one or more types of ventricular tachycardias and fibrillation. Counts of the measured RR intervals which fall into the rate ranges are used to determine whether a tachycardia is present and to diagnose the particular tachyarrhythmia. The detection methodologies practiced in such devices may be difficult for the physician to follow, as the individual intervals may increment or not increment an individual count depending upon factors other than the interval duration alone. For example, rapid onset criteria based upon preceding intervals may be required to continue counting. In some devices, whether a measured R-R interval increments a count, and which count is incremented, may be a function of both the individual interval duration and the average rate over a preceding series of intervals.

In implantable tachyarrhythmia devices, each of the possible diagnoses provided by the device will trigger a predefined therapy, with the general aggressiveness of the therapies increasing from least aggressive if the diagnosis is a slow ventricular tachycardia to most aggressive if the diagnosis is ventricular fibrillation. For example, anti-tachycardia pacing may be employed in response to a diagnosis of slow ventricular tachycardia, cardioversion may be employed if the diagnosis is fast ventricular tachycardia, and defibrillation may be employed if the diagnosis is fibrillation.

Those of ordinary skill in the art will appreciate that with PCDs operable according to complex operational algorithms and in such a variety of modes in which many different device responses may be exhibited, assessment of device operation based only upon observation of the ECG, or even of the ECG in conjunction with conventional event markers, can be difficult. Moreover, a physician or clinician wishing to assess device operation based upon Marker Channel™ event markers may not be familiar with each and every subtle detail of the device's operational algorithm(s), or of its programming and operation, further complicating assessment of device operation.

One advancement related to assisting the physician or clinician in interpreting or assimilating the Marker Channel™ data provided from an implanted device is exemplified in the Elite™ and Elite II™ pacemakers, commercially available from Medtronic, Inc., Minneapolis, Minn. The Elite™ and Elite II™ pacemakers are programmable via a Medtronic Model 9760 programmer, which is capable of converting ten-second traces of Marker Channel™ telemetry data into so-called Marker Channel™ Diagrams, which appear on the programmer's graphical display and may be printed from the programmer's printer. The Marker Channel™ Diagram is an enhancement of the event marker data received via Marker Channel™ telemetry. The diagram is intended to further clarify operation of the pacemaker and simplify analysis of the pacemaker's operation and the patient's ECG. Lines and symbols are provided to represent more details of pacemaker operation. For example, the interrelation of timing intervals, including blanking and refractory intervals, can be revealed in the diagram.

Although improved uplink telemetry systems, provisions for communication of Marker Channel™ data to an external unit, Marker Channel™ diagramming capabilities and the like have alleviated some of the difficulties associated with assessing implanted device performance, it is believed that there remains a need for simplifying the task of interpreting the information provided from an implanted device.

SUMMARY OF THE INVENTION

The present invention, therefore, relates to a method and apparatus for efficiently and effectively conveying information from a hermetically implanted device to a physician or clinician, so that the operation of the device can be accurately assessed.

In one embodiment of the invention, a programming unit for a hermetically implanted device, e.g., a pacemaker, is provided with the capability of presenting Marker Channel™ data to the physician or clinician in an interactive fashion. In particular, the programming unit includes a microprocessor-based computer subsystem executing an expert system software engine. The expert system is supplied with a knowledge base defining the operation of a particular type of implanted device. That is, the expert system is "taught" the implanted device's operational algorithm and programmed parameter settings.

The programming unit is capable of capturing and storing ten second sequences of event marker and ECG data transmitted from the implanted device. On demand, the external unit's expert system processes the data according to the knowledge base of the system.

Further in accordance with the disclosed embodiment, event marker data is displayed in diagrammatic form on the external unit's display. Means are provided for allowing a user to "point to" or select various areas within the event marker diagram. In response to such selection, the external unit displays a context-sensitive explanatory message to the user. The explanatory message will be different depending upon which portion of the event marker diagram the user has selected.

The invention is believed to be particularly advantageous for assisting physicians and clinicians in assessing implanted device operation and efficacy, an in diagnosing patient symptoms. Additionally, the invention is believed to be applicable as an educational tool.

BRIEF DESCRIPTION OF THE DRAWINGS

The foregoing and other aspects and features of the present invention will perhaps be best appreciated with reference to the detailed description of a specific embodiment of the invention which follows, when read in conjunction with the accompanying drawings, wherein.

DETAILED DESCRIPTION OF A SPECIFIC EMBODIMENT OF THE INVENTION

Figure 1:
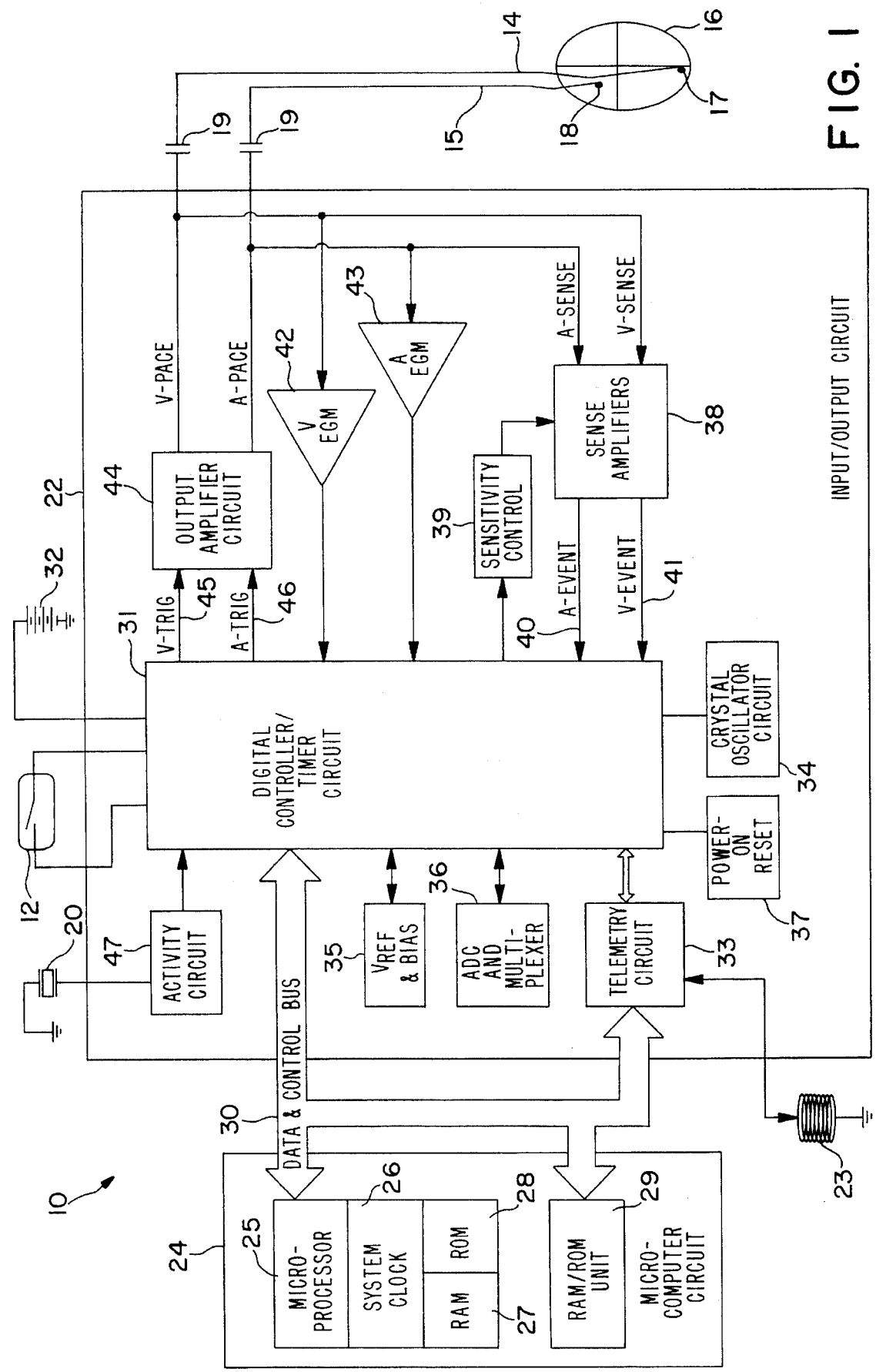
FIG. 1 is a block diagram of an implantable pulse generator in accordance with one embodiment of the present invention.

Referring to FIG. 1, there is shown a block diagram of an implantable pacemaker 10 with which the present invention may be advantageously practiced. Although the present invention will be described herein in the context of pacemaker 10, it is to be understood that the following description is provided merely to illustrate the present invention in its various aspects. It is believed that the present invention may be advantageously practiced in conjunction with various types of implantable devices other than pacemakers, and that those of ordinary skill in the art having the benefit of the present disclosure would be readily able to adapt the disclosed embodiment for incorporation into such other devices.

Moreover, although the present invention will be described herein in conjunction with a pacemaker 10 having a microprocessor-based architecture, it will be understood that pacemaker 10 (or other implanted device) may be implemented in any logic based, custom integrated circuit architecture, if desired.

The pacemaker shown in FIG. 1 is substantially similar to that disclosed in U.S. Pat. No. 5,243,979 to Stein et al., entitled "Method and Apparatus for Implementing Activity Sensing in a Pulse Generator," the Stein '979 patent hereby being incorporated by reference herein in its entirety. Another pacemaker with which the present invention may be advantageously practiced is disclosed in U.S. Pat. No. 5,052,388 to Sivula et al., entitled "Method and Apparatus for Implementing Activity Sensing in a Pulse Generator." The Sivula et al. '388 patent is also hereby incorporated by reference herein in its entirety.

In FIG. 1, pacemaker 10 is shown to include an activity sensor 20, which may be, for example, a piezoelectric element bonded to the inside of the pacemaker's shield. Such a pacemaker/activity sensor configuration is the subject of U.S. Pat. No. 4,485,813 to Anderson et al. Piezoelectric sensor 20 provides a sensor output which varies as a function of a measured parameter that relates to the metabolic requirements of a patient.

Pacemaker 10 of FIG. 1 is programmable by means of an external programming unit 11 (not shown in FIG. 1). One such programmer suitable for the purposes of the present invention is the Medtronic Model 9760 programmer which is commercially available from Medtronic, Inc., and is intended to be used with all Medtronic pacemakers. As noted above, the 9760 programmer is a microprocessor-based device which, for downlink telemetry, transmits a series of encoded signals to an implanted device by means of a programming head which transmits radiofrequency (RF) encoded signals according to the telemetry system laid out, for example, in U.S. Pat. No. 5,127,404 to Wyborny et al. entitled "Telemetry Format for Implanted Medical Device"; which is assigned to the assignee of the present invention and which is incorporated herein by reference in its entirety. For uplink telemetry, the implanted device transmits data using a pulse-position modulation scheme. Uplink telemetry data is transmitted byte-by-byte, with each byte being transmitted as a "frame" containing several RF bursts. The timing of the bursts within a frame indicates the type of data being transmitted, as well as the data itself.

Although specific telemetry systems have been identified herein as being suitable for the purposes of practicing the present invention, it is to be understood, that the present invention is not specific to any one programming methodology. The Wyborny et al. '404 patent is identified herein for the purposes of illustration only, and it is believed that any programming protocol may be employed so long as the desired uplink and downlink information can be conveyed between pacemaker 10 and external programmer 11.

Similarly, it is believed that one of skill in the art would be able to choose from any of a number of available pacemaker programmers and programming techniques to accomplish the tasks necessary for practicing the present invention. As noted above, however, the Medtronic Model 9760 programmer is a presently preferred example.

In the illustrative embodiment of the present invention, parameters such as the lower rate of pacemaker 10 may be programmable, for example from 40 to 90 pulses per minute (PPM) in increments of 10 PPM, and the upper rate may be programmable, for example, between 100 and 175 PPM in 25 PPM increments. Those of ordinary skill in the art will appreciate that other information which may need to be communicated to implantable device in today's state-of-the-art pacemakers includes: pacing mode, multiple rate response settings, electrode polarity, maximum and minimum pacing rates, output energy (output pulse width and/or output current), sense amplifier sensitivity, refractory periods, calibration information, rate response attack (acceleration) and decay (deceleration), onset detection criteria, and perhaps many other parameter settings. The number of programmable parameters increases further for implantable devices, such as PCDs, which are operable in multiple therapy modes.

Pacemaker 10 is schematically shown in FIG. 1 to be electrically coupled via pacing lead 14 and 15 to a patient's heart 16. Leads 14 and 15 include one or more intracardiac electrodes, designated as 17 and 18 in FIG. 1, located near their distal ends of leads 14 and 15, respectively, and positioned within the right ventricular (RV) and right atrial (RA) chambers, respectively, of heart 16. Leads 14 and 15 can be of either the unipolar or bipolar type as is well known in the art; alternatively, a single, multiple-electrode lead may be used.

Electrodes 17 and 18 are coupled via suitable lead conductors through input capacitors 19 to input/output terminals of an input/output circuit 22. In the presently disclosed embodiment, activity sensor 20 is bonded to the inside of the pacemaker's outer protective shield, in accordance with common practice in the art. As shown in FIG. 1, the output from activity sensor 20 is also coupled to input/output circuit 22.

Input/output circuit 22 contains the analog circuits for interface to the heart 16, activity sensor 20, an antenna 23, as well as circuits for the application of stimulating pulses to heart 16 to control its rate as a function thereof under control of the software-implemented algorithms in a microcomputer circuit 24.

Microcomputer circuit 24 comprises a microprocessor 25 having an internal system clock circuit 26, and on-board RAM 27 and ROM 28. Microcomputer circuit 24 further comprises a RAM/ROM unit 29. Microprocessor 25 and RAM/ROM unit 29 are each coupled by a data and control bus 30 to a digital controller/timer circuit 31 within input/output circuit 22. Microcomputer circuit 24 may be a commercially-available, general-purpose microprocessor or microcontroller, or may be a custom integrated circuit device augmented by standard RAM/ROM components.

It will be understood that each of the electrical components represented in FIG. 1 is powered by an appropriate implantable battery power source 32, in accordance with common practice in the art. For the sake of clarity, the coupling of battery power to the various components of pacemaker 10 has not been shown in the Figures.

An antenna 23 is connected to input/output circuit 22 for purposes of uplink/downlink telemetry through an RF telemetry circuit 33. In the embodiment of FIG. 1, telemetry circuit 33 is coupled to digital controller/timer circuit 31, and includes circuitry generally in accordance with that disclosed in the above-referenced Markowitz '382 patent, such that event markers indicative of the occurrence of certain physiologic and pacer events may be transmitted to external programming unit 11. It is contemplated that telemetry circuit 33 may also be coupled directly to microcomputer circuit 24 via data and control bus 30.

A reed switch 12 is also coupled to input/output circuit 22. Although reed switch closure is no longer employed as the primary means of non-invasively communicating with an implanted device, reed switches are often still included in implantable devices as a supplement to the telemetry system. For example, reed switch closure may be required before a telemetry link can be established, as a safeguard against spurious programming of the device. Reed switch closure may also cause the device to enter into a default mode of operation, sometimes referred to as "magnet mode," so that device operation remains consistent during programming or interrogation sessions.

A crystal oscillator circuit 34, typically a 32,768-Hz crystal-controlled oscillator, provides main timing clock signals to digital controller/timer circuit 31. A $V_{REF}$ and Bias circuit 35 generates stable voltage reference and bias currents for the analog circuits of input/output circuit 22. An analog-to-digital converter (ADC) and multiplexer unit 36 digitizes analog signals and voltages to provide "real-time" telemetry intracardiac signals and battery end-of-life (EOL) replacement function. A power-on-reset (POR) circuit 37 functions as a means to reset circuitry and related functions to a default condition upon detection of a low battery condition, which will occur upon initial device power-up or will transiently occur in the presence of electromagnetic interference, for example.

The operating commands for controlling the timing of pacemaker 10 are coupled by bus 30 to digital controller/timer circuit 31 wherein digital timers and counters are employed to establish the overall escape interval of the pacemaker, as well as various refractory, blanking, and other timing windows for controlling the operation of the peripheral components within input/output circuit 22.

Digital controller/timer circuit 31 is coupled to sensing circuitry including a sense amplifier circuit 38 and a sensitivity control circuit 39. In particular, digital controller/timer circuit 31 receives an A-EVENT (atrial event) signal on line 40, and a V-EVENT (ventricular event) signal on line 41. Sense amplifier circuit 38 is coupled to leads 14 and 15, in order to receive the V-SENSE (ventricular sense) and A-SENSE (atrial sense) signals from heart 16. Sense amplifier circuit 38 asserts the A-EVENT signal on line 40 when an atrial event (i.e., a paced or intrinsic atrial event) is detected, and asserts the V-EVENT signal on line 41 when a ventricular event (paced or intrinsic) is detected. Sense amplifier circuit 38 includes one or more sense amplifiers corresponding, for example, to that disclosed in U.S. Pat. No. 4,379,459 issued to Stein on Apr. 12, 1983, incorporated by reference herein in its entirety.

Sensitivity control 39 is provided to adjust the gain of sense amplifier circuitry 38 in accordance with programmed sensitivity settings, as would be appreciated by those of ordinary skill in the pacing art.

A V-EGM (ventricular electrocardiogram) amplifier 42 is coupled to lead 14 to receive the V-SENSE signal from heart 16. Similarly, an A-EGM (atrial electrocardiogram) amplifier 43 is coupled to lead 15 to receive the A-SENSE signal from heart 16. The electrogram signals developed by V-EGM amplifier 42 and A-EGM amplifier 43 are used on those occasions when the implanted device is being interrogated by external programmer 11, to transmit by uplink telemetry a representation of the analog electrogram of the patient's electrical heart activity, such as described in U.S. Pat. No. 4,556,063, issued to Thompson et al., assigned to the assignee of the present invention and incorporated herein by reference.

Digital controller and timer circuit 31 is coupled to an output amplifier circuit 44 via two lines 45 and 46, designated V-TRIG (ventricular trigger) and A-TRIG (atrial trigger), respectively. Circuit 31 asserts the V-TRIG signal on line 45 in order to initiate the delivery of a ventricular stimulating pulse to heart 16 via pace/sense lead 14. Likewise, circuit 31 asserts the A-TRIG signal on line 46 to initiate delivery of an atrial stimulating pulse to heart 16 via pace/sense lead 15. Output amplifier circuit 44 provides a ventricular pacing pulse (V-PACE) to the right ventricle of heart 16 in response to the V-TRIG signal developed by digital controller/timer circuit 31 each time the ventricular escape interval times out, or an externally transmitted pacing command has been received, or in response to other stored commands as is well known in the pacing art. Similarly, output amplifier circuit 44 provides an atrial pacing pulse (A-PACE) to the right atrium of heart 16 in response to the A-TRIG signal developed by digital controller/timer circuit 31. Output amplifier circuit 44 includes one or more output amplifiers which may correspond generally to that disclosed in U.S. Pat. No. 4,476,868 issued to Thompson on Oct. 16, 1984 also incorporated herein by reference in its entirety.

As would be appreciated by those of ordinary skill in the art, input/output circuitry will include decoupling circuitry for temporarily decoupling sense amplifier circuit 38, V-EGM amplifier 45 and A-EGM amplifier 46 from leads 14 and 15 when stimulating pulses are being delivered by output amplifier circuit 44. For the sake of clarity, such decoupling circuitry is not depicted in FIG. 2.

While specific embodiments of sense amplifier circuitry, output amplifier circuitry, and EGM amplifier circuitry have been identified herein, this is done for the purposes of illustration only. It is believed by the inventor that the specific embodiments of such circuits are not critical to the present invention so long as they provide means for generating a stimulating pulse and provide digital controller/timer circuit 31 with signals indicative of natural and/or stimulated contractions of the heart. It is also believed that those of ordinary skill in the art could chose from among the various well-known implementations of such circuits in practicing the present invention.

Digital controller/timer circuit 31 is coupled to an activity circuit 47 for receiving, processing, and amplifying activity signals received from activity sensor 20. A suitable implementation of activity circuit 47 is described in detail in the above-referenced Sivula et al. application. (It is to be understood that the inclusion of an activity circuit in pacemaker 10 is not an essential feature of the present invention. The presence of an activity circuit is noted herein as but one example of the sophisticated operational capabilities of state-of-the-art implanted devices which make the devices' responses to physiological conditions complex and difficult to interpret.)

Figure 2:
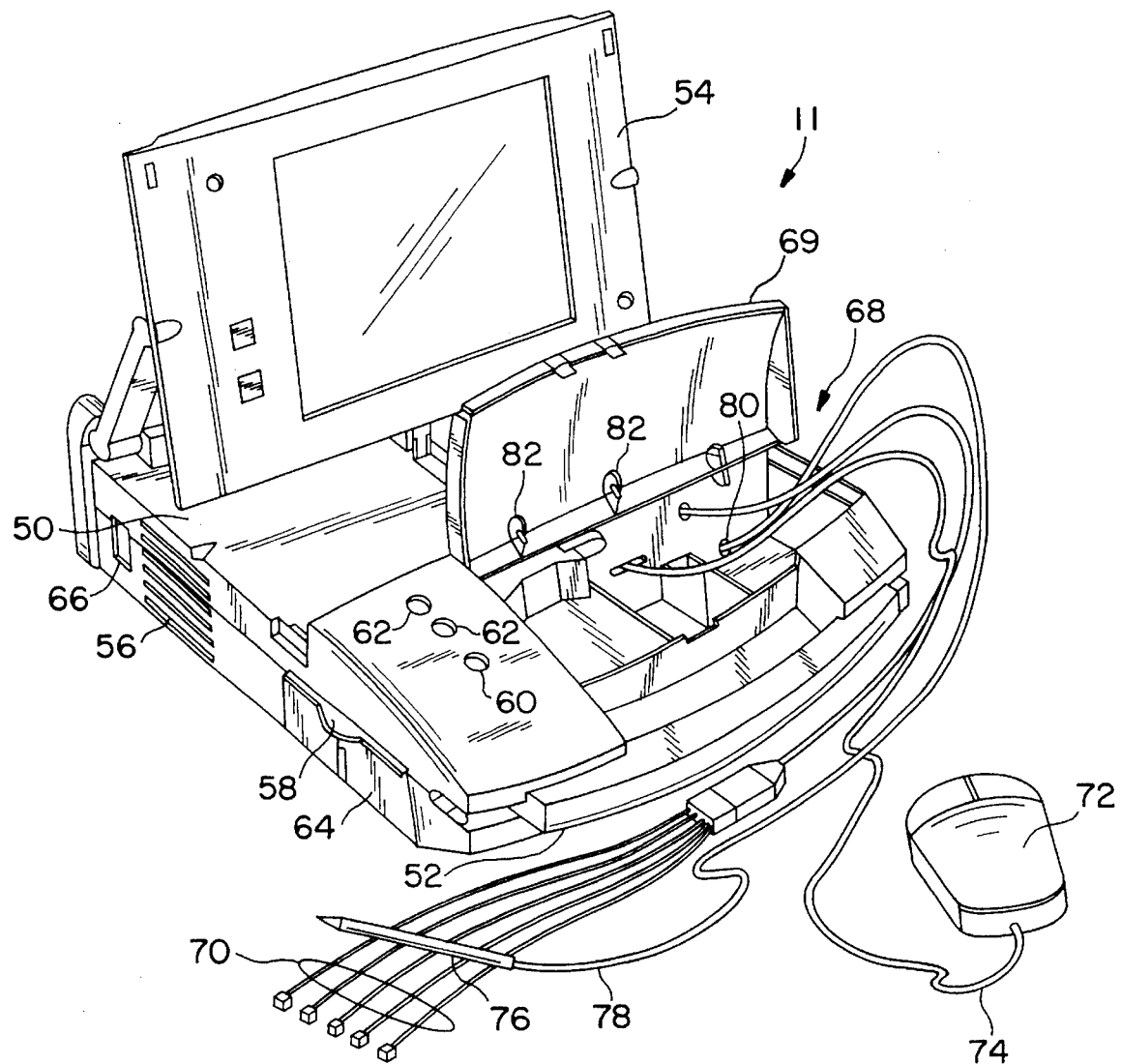
FIG. 2 is a perspective view of an external programming unit in accordance with the disclosed embodiment of the invention, used for communicating with the pulse generator of FIG. 1.

In accordance with conventional practice, pacemaker 10 from FIG. 1 communicates via RF telemetry with an external programming unit 11, an example of which is illustrated in FIG. 2. Internally, programmer 11 includes a processing unit (not shown in the Figures) which in accordance with the presently disclosed embodiment of the invention is a personal computer type motherboard, e.g., a computer motherboard including an Intel 80386 microprocessor and related circuitry such as digital memory. The details of design and operation of the computer system will not be set forth in detail in the present disclosure, as it is believed that such details are well-known to those of ordinary skill in the art. For the purposes of the present disclosure, it suffices to state that programmer 11 is capable of performing at least the types of operations of which the Medtronic Model 9760 programmer is capable.

Referring to FIG. 2, programmer 11 comprises an outer housing 50, which is preferably made of thermal plastic or another suitably rugged yet relatively lightweight material. A carrying handle, designated generally as 52 in FIG. 2, is integrally formed into the front of housing 50. With handle 52, programmer 11 can be carried like a briefcase.

An articulating display screen 54 is disposed on the upper surface of housing 50. Display screen 54 folds down into a closed position (not shown) when programmer 11 is not in use, thereby reducing the size of programmer 11 and protecting the display surface of display 54 during transportation and storage thereof.

A floppy disk drive is disposed within housing 50 and is accessible via a disk insertion slot (not shown). A hard disk drive is also disposed within housing 50, and it is contemplated that a hard disk drive activity indicator, (e.g., an LED, not shown) could be provided to give a visible indication of hard disk activation.

As would be appreciated by those of ordinary skill in the art, it is often desirable to provide a means for programmer 11 to adapt its mode of operation depending upon the type of implanted device to be programmed. Accordingly, it may be desirable to have an expansion cartridge containing EPROMs or the like for storing program information to control programmer 11 to operate in a particular manner corresponding to a given type of implantable device.

Air vents 56 are provided at various points in housing 50, so that an internal fan (not shown) can circulate air within housing 50 and prevent overheating of components therein. In addition, a printer output slot 58 is disposed on the left side of housing 50. In accordance with the presently preferred embodiment of the invention, programmer 11 is equipped with an internal printer (not shown) so that a hard-copy of a patient's ECG or of graphics displayed on the programmer's display screen 54 can be generated. Several types of printers, such as the AR-100 printer available from General Scanning Co., are known and commercially available. A printer control button 60 and printer speed control buttons 62 are disposed on the upper surface of housing 50 so that the printer can be activated and the speed of stripchart output selected. Buttons 60 and 62 are preferably of the well-known membrane type or are otherwise sealed such that external moisture and dirt are repelled.

A hinged cover 64 can be opened to provide access to the internal printer mechanism, e.g., to supply the printer with paper. Also shown in FIG. 2 is a power switch 66 which is preferably inset slightly with respect to housing 50, such that the likelihood of accidentally turning programmer 11 off is minimized.

In the perspective view of FIG. 2, programmer 11 is shown with articulating display screen 54 having been lifted up into one of a plurality of possible open positions such that the display area thereof is visible to a user situated in front of programmer 11. Articulating display screen is preferably of the LCD or electroluminescent type, characterized by being relatively thin as compared, for example, a cathode ray tube (CRT) or the like. In the presently preferred embodiment of the invention, display screen 54 is one manufactured by and commercially available from Planar Systems, Inc., although it is contemplated that any of the various types of computer graphics display screens would be suitable for the purposes of the present invention.

As would be appreciated by those of ordinary skill in the art, display screen 54 is operatively coupled to the computer circuitry disposed within housing 50 and is adapted to provide a visual display of graphics and/or data under control of the internal computer.

Display screen 54 may provided with touch-sensitive capability, such that a user can interact with the internal computer by touching the display area of display screen 54 with a stylus, or even the user's finger. It is believed that those of ordinary skill in the art will be familiar with touch-sensitive display technology, and the details of implementation of such a display will not be described further herein. Touch-sensitive display screen 54 is the primary input medium for programmer 11, and therefore preferably has sufficient resolution to support stylus operations including selection, gestures, annotation, and character recognition.

With continued reference to FIG. 2, a compartment 68 with a hinged cover 69 is provided generally near the front of programmer 11. Compartment 68 is used for storage of a programming head 72 which, as would be appreciated by those of ordinary skill in the art, is placed over a patient's body near the implant site of an implanted device, in order to establish a telemetry link between the implanted device and the programmer. Such a programming head is disclosed, for example, in the above-reference Hartlaub programmer patents. Programming head 72 is coupled to internal circuitry of programmer 11 via a cable 74.

Compartment 68 is also used for storage of a stylus 76 used to interact with touch screen 54. Stylus 76 is coupled to circuitry within housing 50 via a cable 78 that is coupled to programmer 11 by means of a coaxial connector 80. Clips 82 are preferably provided on the underside of hinged cover 69 for holding stylus 76 when not in use. Alternatively, programmer 11 may be equipped with a conventional computer "mouse"-type pointing device (not shown), rather than stylus 76, for user interaction with touch screen 54. In the absence of either a stylus or a mouse, on-screen cursor control for enabling user interaction with programmer 11 may be facilitated through cursor control keys (arrow keys or the like, not shown in FIG. 2) disposed on programmer 11.

Compartment 68 is also used for storage of a plurality patient cables 70 for obtaining a patient's surface ECG. Patient cables 70 convey a patient's surface ECG to internal circuitry of programmer 11, so that the surface ECG can be displayed on display screen 54 or printed out on the internal printer, as previously described.

Programmer 11 described herein with reference to FIG. 2 is described in more detail in copending U.S. patent application Ser. No. 08/055,072, filed in the name of Thomas J. Winkler, entitled "Portable Computer Apparatus With Articulating Display Panel," which patent is hereby incorporated herein by reference in its entirety. Also, as previously noted, the Medtronic Model 9760 programmer is another implantable device programming apparatus with which the present invention may be advantageously practiced.

When in telemetric contact with an implantable device, the Model 9760 programmer is capable of capturing and storing ten-second intervals of ECG data and the corresponding Marker Channel™ data transmitted from the implanted device. Additionally, the Model 9760 is capable of displaying the ECG data and a corresponding Marker Channel™ Diagram on its display screen. In accordance with an important feature of the present invention, programmer 11 is similarly capable of capturing and displaying patient ECG and Marker Channel™ data, and of generating and displaying Marker Channel™ Diagrams based upon the Marker Channel™ data.

Figure 3:
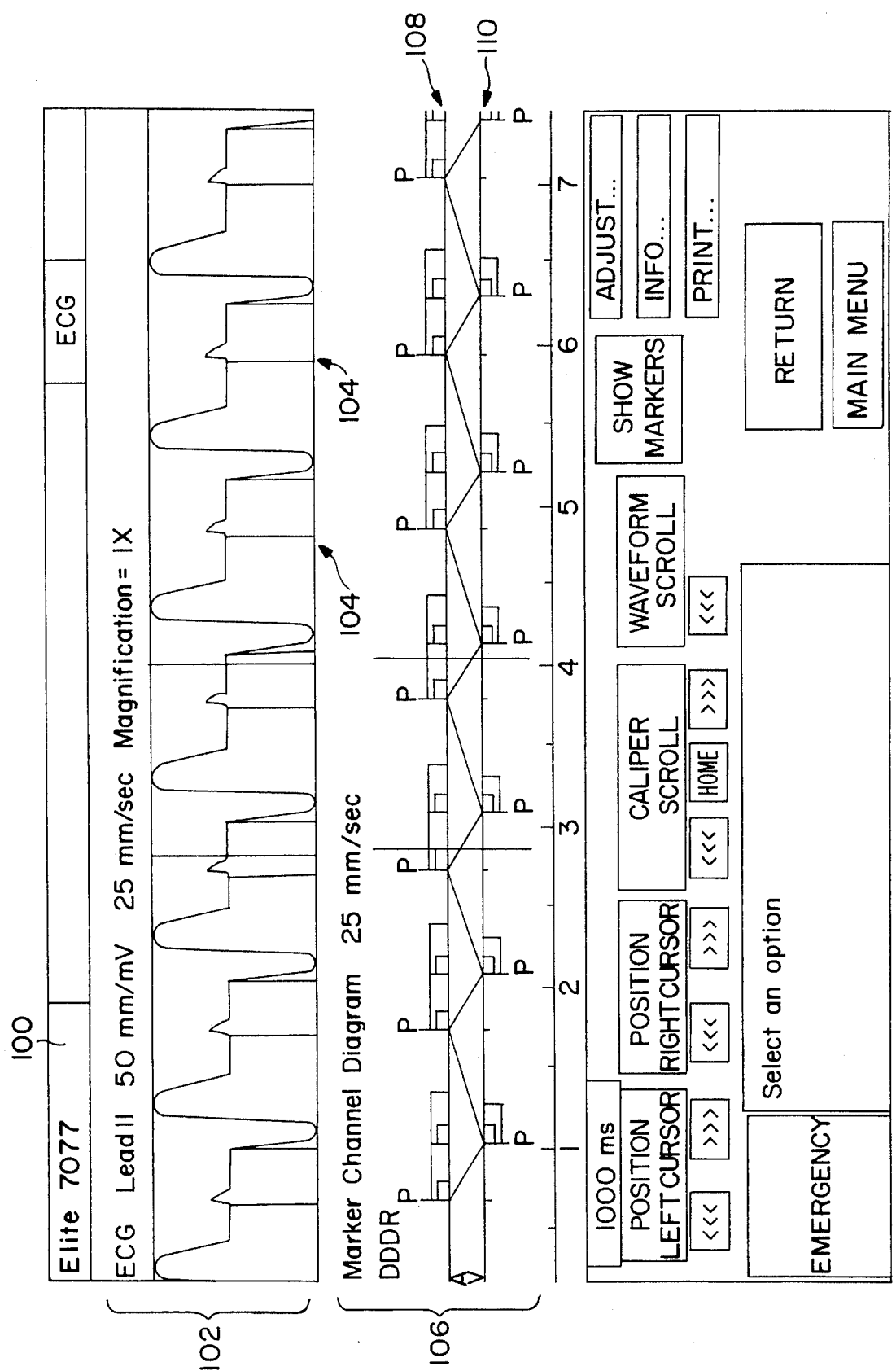
FIG. 3 is an illustration of an image displayed on the display screen of the programming unit of FIG. 2.

An example of an ECG waveform and Marker Channel™ Diagram as it is displayed on the Model 9760 programmer's screen and on display screen 54 of programmer 11 in the presently disclosed embodiment of the invention is shown in FIG. 3. In the upper left-hand corner of the Marker Channel™ Diagram screen of FIG. 3, the implanted device with which programmer 11 is presently in communication is identified, in a device identifier field 100. As previously noted, programmer 11 is preferably capable of communicating with more than one type or model of implanted device, and its programming capabilities may be altered either by initiating execution of different software stored in programmer 11 (e.g., stored on the programmer's internal hard disk drive) or by insertion of a device-specific EPROM module into the expansion slot of programmer 11, previously described with reference to FIG. 2.

In an ECG field 102, a ten-second portion of patient ECG data is displayed. This ECG data may be derived from a real-time ECG signal transmitted from implanted device 10, or alternatively may be derived from a surface ECG obtained using patient cables 70 of programmer 11. Also appearing in ECG field 102 are pacing artifacts, such as those designated 104 in FIG. 3.

Below ECG field 102 is a Marker Channel™ Diagram field 106. Each Marker Channel™ Diagram is formed by a series of lines and symbols that depict pacemaker operation.

Figure 4:
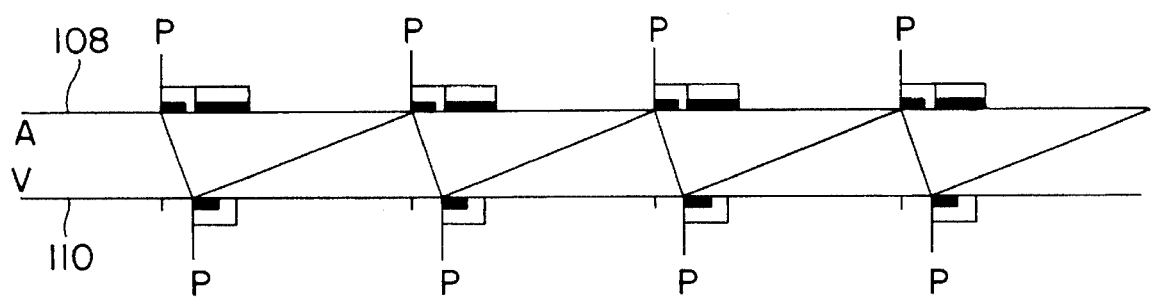
FIG. 4 is an illustration of an event marker diagram portion of the image from FIG. 3.

For clarity, a sample Marker Channel" Diagram is shown in isolation in FIG. 4. The Marker Channel™ Diagram is formed along two parallel base lines 108 and 110. This is also shown in the portion of a Marker Channel™ Diagram shown in FIG. 5a. Symbols depicting atrial events appear along the top side of baseline 108, while symbols depicting ventricular events appear along the bottom side of baseline 110. Between baselines 108 and 110 is a diagram depicting the timing relationship between atrial and ventricular events.

Figure 5A:
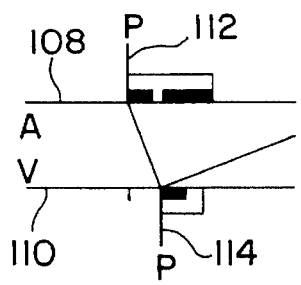
FIGS. 5a through 5g are illustrations of portions of event marker diagrams similar to that from FIG. 4.

Referring to FIG. 5a, short vertical lines, such as that designated with reference numeral 112 which extends upward from atrial baseline 108 and that designated with reference numeral 114 which extends downward from ventricular baseline 110, represent event markers received via Marker Channel™ telemetry.

Figure 5B:
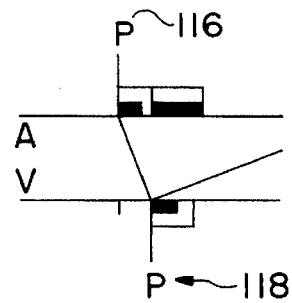

As identified in FIG. 5b, labels, such as those designated with reference numerals 116 and 118 are associated with each marker to indicate the event it represents. A listing of the labels used to identify Marker Channel™ events in the Marker Channel™ Diagram is set forth in the following Table 1:

TABLE 1

| LABEL | EVENT |
|-------|-------|
| P  | (Pace) -- Output of a pacing stimulus |
| S  | (Sense) -- A sensed event |
| R  | (Refractory Sense) -- An event sensed within the refractory period |
| ER | (Error) -- A marker that could not be decoded because of interference or interrupted telemetry reception |

For example, in FIG. 5b, "P" label 116 indicates an atrial pace event, while "P" label 118 indicates a ventricular pace event.

Figure 5C:
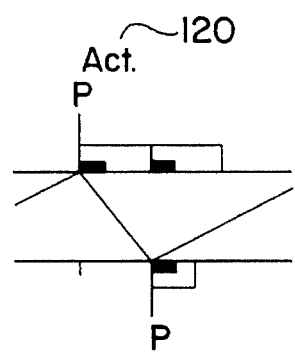

Turning to FIG. 5c, supplemental labels, such as the "ACT" label 120, are provided to indicate when a marker is the result of certain specified conditions, as set forth in the following Table 2

TABLE 2

| SUPPLEMENTAL LABEL | CONDITION |
|--------------------|-----------|
| ACT  | An activity-driven atrial Pace |
| SAFE | A ventricular Safety Pace |
| PVC  | A ventricular Sense or ventricular Refractory Sense defined by the pacemaker as a premature ventricular contraction |

(The inclusion of so-called "supplemental" codes in the Marker Channel™ data stream is described in greater detail in co-pending U.S. patent application Ser. No. 08/010,970 filed in the name of Keimel and entitled "Diagnostic Telemetry System for an Apparatus for Detection and Treatment of Tachycardia and Fibrillation". The '970 application is hereby incorporated herein by reference in its entirety.)

Figure 5D:
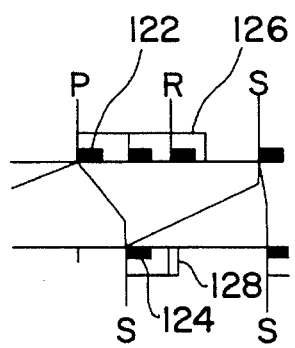

As shown in FIG. 5d, solid rectangles, such as those designated with reference numerals 122 and 124, and open rectangles, such as those designated with reference numerals 126 and 128, depict various timing periods of relevance to pacemaker operation. In particular, solid rectangles on baselines 108 and 110 indicate atrial and ventricular blanking periods, respectively, while open rectangles on baselines 108 and 110 indicate atrial and ventricular refractory periods, respectively.

Figure 5E:
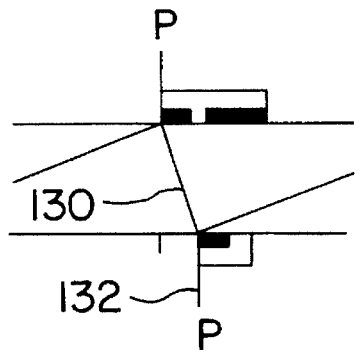

Sloped, horizontal, and vertical lines appearing between atrial baseline 108 and ventricular baseline 110 depict timing relationships between atrial and ventricular events. Referring to FIG. 5e, downward-sloping lines, such as that designated with reference numeral 130, depict atrial-to-ventricular (A-to-V) timing (based on the programmed AV interval) initiated by an atrial Pace or Sense event. The course of downward-sloping lines results in a ventricular pace (e.g., vertical line 132 in FIG. 5e) unless it is interrupted by a ventricular sense, as will be hereinafter described.

Figure 5F:
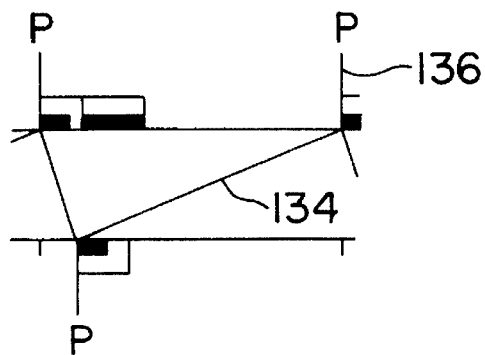

Upward-sloping lines, such as the one designated with reference numeral 134 in FIG. 5f, represent ventricular-to-atrial (V-to-A) timing (based on the programmed Lower Rate) initiated by a ventricular Pace or Sense event. The course of upward sloping lines results in an atrial pace (e.g., vertical line 136 in FIG. 5f) unless it is interrupted by an atrial Sense or an Activity driven (ACT) atrial Pace.

Figure 5G:
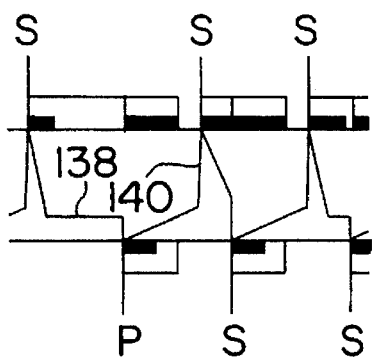

Horizontal lines, such as that designated with reference numeral 138 in FIG. 5g, indicates any extension in the V-to-A timing required to maintain a proper Pace schedule. Vertical lines, such as that designated with reference numeral 140 in FIG. 5g, shows the interruption of a timing interval by a Sense or Activity Pace.

Marker Channel™ Diagrams also depict certain additional error conditions and special conditions (such as the occurrence of diagnostic tests and the like). The particular manner in which such conditions are depicted will not be described herein in detail, as this is not considered critical to an understanding of the present invention.

In accordance with an important feature of the present invention, the ECG waveform and Marker Channel™ Diagram similar to that shown in FIG. 3 that is displayed on text/graphics display screen 54 of programmer 11 is an interactive screen. That is, utilizing a cursor control device such as stylus 76 (or, alternatively, a mouse or cursor control buttons), a physician or clinician viewing the Marker Channel™ Diagram can elicit explanatory messages about various aspects of the Marker Channel™ Diagram.

Specifically, in accordance with the presently disclosed embodiment of the invention, software executed by programmer 11 defines a plurality of regions ("hotspots") within the area of the Marker Channel™ Diagram, each such region being associated with a particular aspect of the diagram. Then, when the physician or clinician identifies a particular regions, such as by touching display screen 54 with stylus 54, or by a "point and click" action with a mouse, explanatory text about the corresponding portion of the Marker Channel™ Diagram temporarily appears on the screen.

Figure 6:
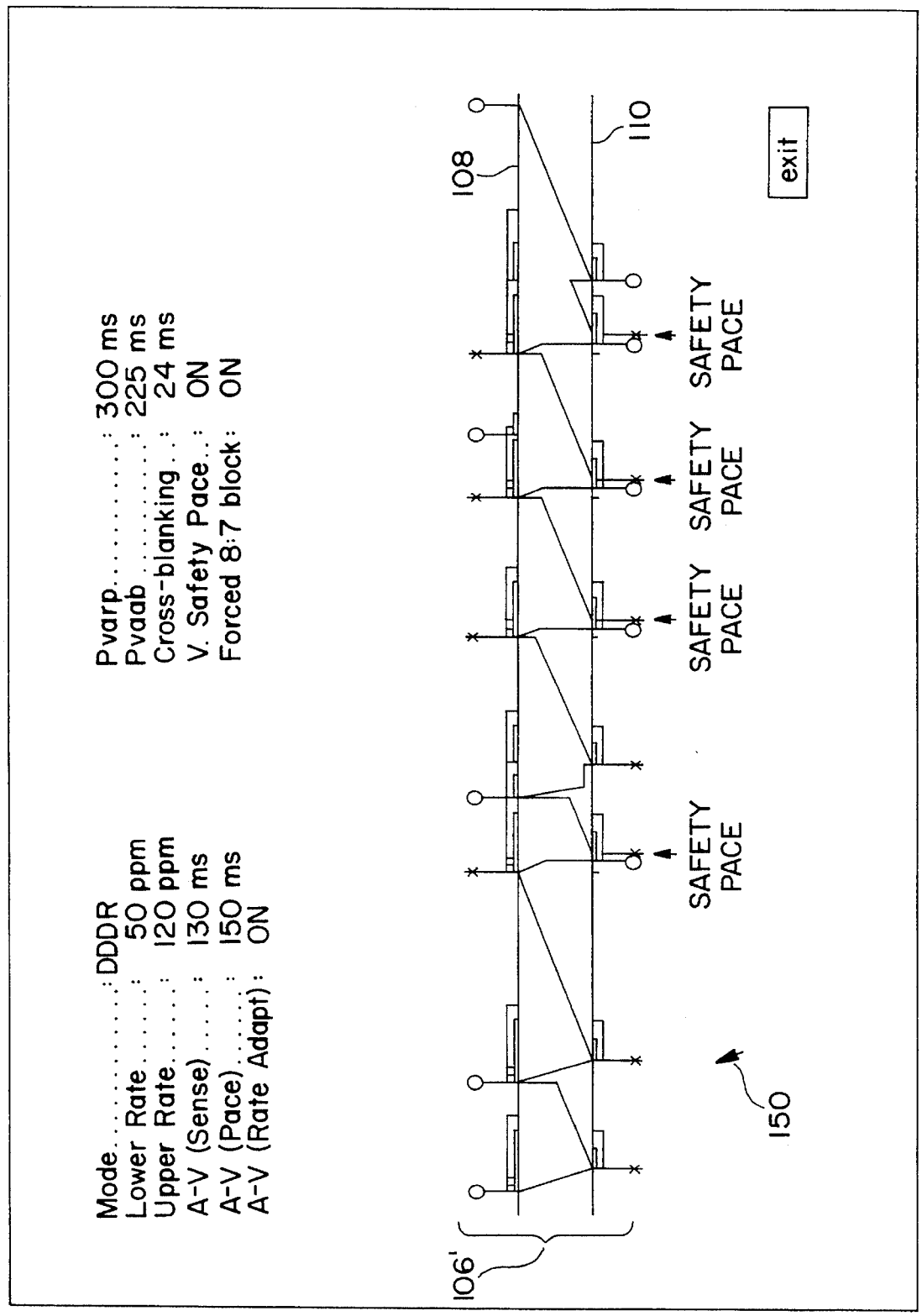
FIG. 6 is an illustration of an image displayed on the display screen of the programming unit of FIG. 2, in accordance with the disclosed embodiment of the invention.

An example of the interactive Marker Channel™ Diagram feature in accordance with the presently disclosed embodiment of the present invention is depicted in FIG. 6. In particular, FIG. 6 depicts an example of a Marker Channel™ Diagram screen which is displayed on text/graphics display screen 54 of programmer 11. In the Marker Channel™ Diagram field 106' in the example of FIG. 6, a conventional Marker Channel™ Diagram is displayed.

Also shown in FIG. 6 is a cursor, designated with reference numeral 150, whose position is controlled in a conventional manner, i.e., with a mouse or cursor control keys on programmer 11. (As will be appreciated by those of ordinary skill in the art, cursor 150 may not be necessary if stylus 76 is used by the physician or clinician to identify a particular location on text/graphics display screen 54.)

Figure 7:
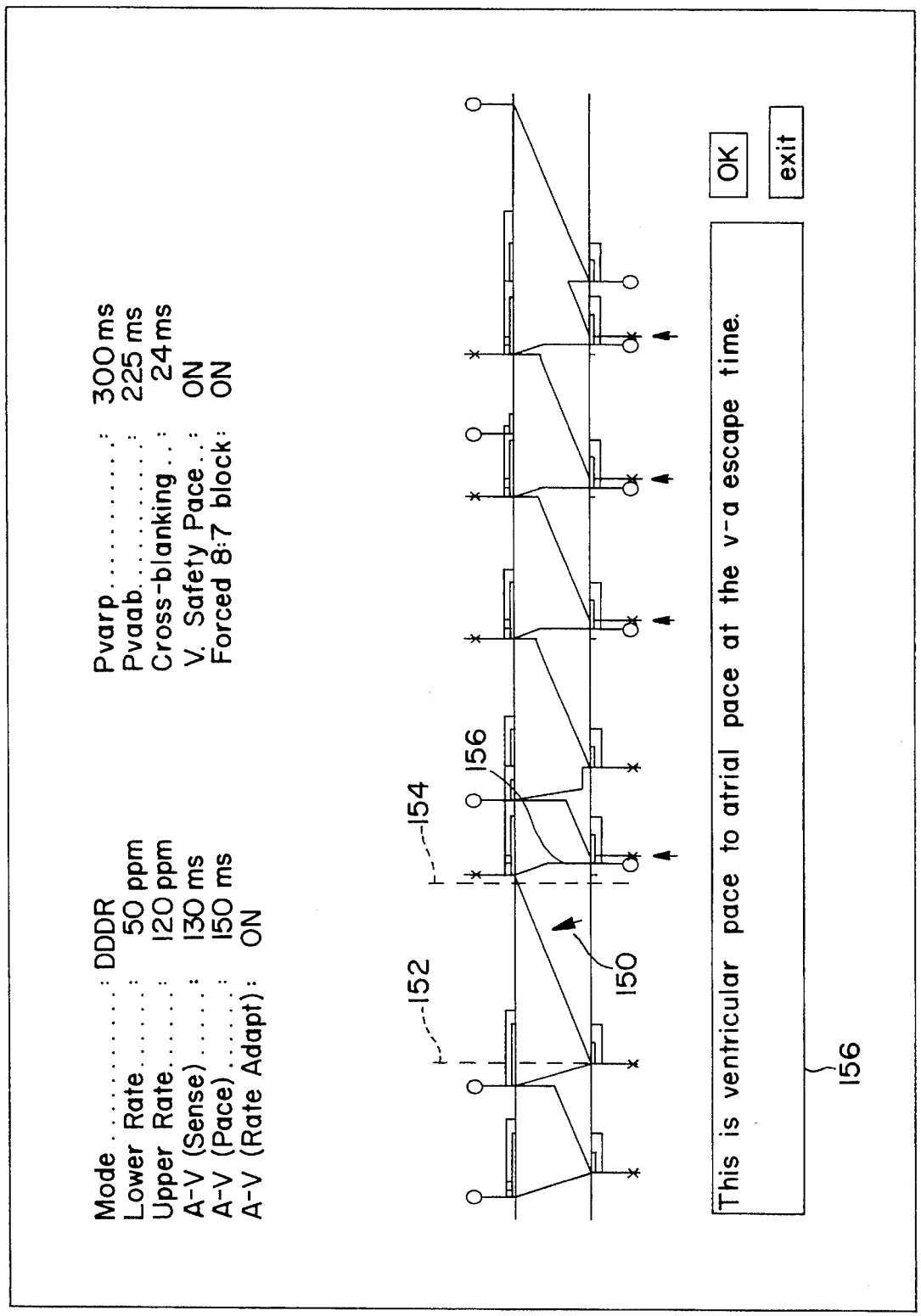
FIG. 7 is another illustration of an image displayed on the display screen of the programming unit of FIG. 2, showing an explanatory text section in accordance with the disclosed embodiment of the invention.

In the course of deriving the Marker Channel™ Diagram to be displayed, programmer 11 defines various separate areas of the diagram, each associated with a physiologic or pacer event. In the presently disclosed embodiment of the invention, for example, the Marker Channel™ Diagram is divided into a series of sections arranged horizontally along the diagram, each section beginning at a particular physiologic or pacer event and extending horizontally to another such event. Referring now to FIG. 7, one such section begins at a horizontal location indicated with dashed line 152 and ends at a horizontal location indicated with dashed line 154. From the Marker Channel™ Diagram, it can be seen that horizontal location 152 is associated with a Ventricular Pace event, while horizontal location 154 is associated with an Atrial Pace event.

When a point situated between horizontal locations 152 and 154 is selected, for example, by touching display screen 54 with stylus 76, or by "pointing and clicking" with a mouse, programmer 11 causes an explanatory text box, designated with reference numeral 156 in FIG. 7. The text in box 156 explains what situation is represented by the Marker Channel™ Diagram in the section selected by the user. In the particular example depicted in FIG. 7, the section selected (between horizontal locations 152 and 154) is an upward-sloping line between a Ventricular Pace event and an Atrial Pace event. Accordingly, the text in box 156 indicates that "This is ventricular pace to atrial pace at the v-a escape time."

In accordance with the disclosed embodiment of the invention, selection of different points along the Marker Channel™ Diagram will cause different messages will be displayed. For example, if the point designated with reference numeral 156 in FIG. 7 is selected, the following message appears in box 156: "This is atrial pace to ventricular sense inside the Safety Pace window of 110 milliseconds. It will cause a ventricular pace at an A-V interval of 110 milliseconds." As will be appreciated by those of ordinary skill in the art, such explanatory text can be of considerable benefit to a physician or clinician attempting to interpret the Marker Channel™ Diagram. The explanatory messages in box 156 can also contain "hypertext" links to additional informational messages, further explaining the meaning of particular words or phrases used in the explanatory text itself. It is believed that the realization of such "hypertext" links would be a matter of routine software design to those of ordinary skill in the computer art.

Examples of "hypertext" messages which may be linked to text within box 156 are provided in Table 6 below.

In the presently preferred embodiment of the invention, the messages displayed in box 156 on display 54 are generated by programmer 11 executing expert system software, such as the VP-Expert™ rule-based expert system engine (the 1987 copyright to which is owned by Paperback Software International, 2830 Ninth Street, Berkeley, Calif.). Various expert system software packages are known and commercially available, and it is believed that those of ordinary skill in the art having the benefit of the present disclosure would be able to select an suitable one for the purposes of practicing the present invention.

In the presently preferred embodiment of the invention, the expert system engine is initially provided with a set of "rules" specific to a particular model of implanted device operating in a particular mode, these rules defining a so-called "knowledge base" for the expert system. For example, one knowledge base is provided for the Elite™ device operating in DDDR mode. In operation, the expert system engine is provided with a collection of uplink data associated with a ten-second interval of device operation. This data, in the presently disclosed embodiment of the invention, includes: the device type, the programmed operating parameters of the device (e.g., the mode, the lower and upper rate settings, the A-V interval, etc. . . . ), and the Marker Channel™ data transmitted by the device during the ten-second interval. The expert system engine then processes the data according to the predetermined "rules," i.e., it applies the knowledge base to the data, in order to define the various sections of the Marker Channel™ Diagram and the explanatory text associated with each of those sections.

The following exemplary VP Expert™ knowledge bases are made a part of the present application in the form of microfiche appendices:

Appendix 1: Elite™ operating in DDD mode
Appendix 2: Elite™ operating in DDDR mode
Appendix 3: Elite™ operating in DDI mode
Appendix 4: Elite™ operating in DDIR mode
Appendix 5: Elite™ operating in DOO mode
Appendix 6: Elite™ operating in DOOR mode
Appendix 7: Elite™ operating in DVI mode
Appendix 8: Elite™ operating in DVIR mode Those of ordinary skill in the art will appreciate that the knowledge base for a particular device operating in a particular mode essentially encompasses the device's operational algorithm for that mode.

It is to be understood that although the exemplary knowledge bases appended hereto relate to pacemakers operable in dual-chamber pacing modes, the present invention may be similarly advantageously practiced in connection with single-chamber pacing modes.

An example of the marker channel data that is supplied from implanted device 10 to programmer 11 for processing by the expert system is shown in the following Table 3:

TABLE 3

| MARKER EVENT NUMBER | MARKER EVENT | TIME OF EVENT (msec) |
|---|---|---|
| 1 | AS | 100 |
| 2 | AS | 150 |
| 3 | VP | 280 |
| 4 | AS | 760 |
| 5 | VP | 890 |
| 6 | AP | 1940 |
| 7 | VS | 2010 |
| 8 | VP | 2050 |
| 9 | AS | 2360 |
| 10 | VP | 2550 |
| 11 | AP | 3290 |
| 12 | VS | 3350 |
| 13 | VP | 3400 |
| 14 | AP | 4100 |
| 15 | VS | 4160 |
| 16 | VP | 4210 |
| 17 | ASR | 4460 |
| 18 | AP | 4910 |
| 19 | VS | 4970 |
| 20 | VP | 5020 |
| 21 | VS | 5330 |
| 22 | AS | 6330 |
| 23 | XX | 6400 |
| 24 | XX | 6400 |

As previously noted, the programmed device parameters are also provided to the programmer for processing by the expert system. These parameters are routinely supplied to the programmer whenever a telemetry link is established.

In the embodiment of the invention described herein, the expert system defines linear, horizontal sections of the Marker Channel™ Diagram and assigns particular explanatory textual passages to them. It is contemplated, however, that the sections or "hot-spots" defined by the expert system need not be strictly linear. For example, it is contemplated that separate "hot-spot" areas, corresponding to the refractory and blanking rectangles, could be defined, so that a physician or clinician who is unsure of the reason(s) for and effects of the presence of these intervals could select one of the rectangles and be presented with appropriate explanatory text. In this case, separate sections of the Marker Channel™ Diagram, corresponding to the refractory and blanking interval rectangles above atrial baseline 108 and ventricular baseline 110 would be defined apart from the sections between baselines 108 and 110 defined as described above. Thus, the present invention is not believed to be limited in the shape, configuration, and arrangement of the "hot-spots" defined by the expert system.

Moreover, it is contemplated that different knowledge bases could be provided to the expert system software for a given model of implanted device, with the different knowledge bases directed to physicians or clinicians of different levels of familiarity with the device and its operation, or to physicians or clinicians having different intentions in using the Marker Channel™ Diagram. For example, a knowledge base for a person with a high degree of familiarity with the implanted device could be such that the explanatory text presented during an interactive Marker Channel™ Diagram session focuses on more of the subtleties and details of operation, while the knowledge base for a person who is less familiar with the device and its operation could be such that the explanatory text presented during an interactive session describes the diagram in more simplified terms. Similarly, different knowledge bases might be used for the same device depending upon whether the physician is attempting to optimize device parameters for a patient or instead is attempting to troubleshoot an apparent malfunction of the device itself or merely to educate himself regarding operation of the device. In general, it is contemplated that the level of expertise of the user, the intended nature of the interactive sessions to be carried out, and perhaps other factors may be taken into account in preparing the knowledge base for the expert system.

An example of the collection of explanatory messages which might appear during an interactive Marker Channel™ Diagram session in accordance with the presently disclosed embodiment of the invention is set forth in the following Table 5:

TABLE 5

EXPLANATORY TEXT

This is prestarting state.
This is starting with atrial sense to ventricular pace.
This is starting with atrial pace to ventricular pace.
This is starting with ventricular sense refractory to ventricular pace.
This is starting with atrial pace to ventricular sense.
This is starting with ventricular pace to ventricular sense.
This is starting with ventricular pace to ventricular sense in refractory, with Safety Pace programmed OFF.
This is starting with ventricular pace to ventricular sense refractory.
This is starting with atrial sense to two consecutive ventricular senses. This qualifies as a PVC.
This is starting with ventricular pace to ventricular sense, including an intervening atrial sense refractory.
This is starting with ventricular pace to ventricular sense refractory, including an intervening atrial sense refractory.
This is continuing to read markers after an interruption.
This is atrial sense to atrial sense refractory within the AV (Sense) interval.
This is atrial sense to atrial sense refractory. The AV (Sense) interval is extended to prevent pacing faster than the programmed upper rate.
This is atrial sense to atrial sense refractory. The AV (Sense) interval is shortened to 65 ms due to a prior atrial event within 500 ms. The AV is extended to prevent pacing faster than the upper rate.
This is atrial sense to ventricular sense.
This is atrial sense to ventricular sense. The AV interval is extended to prevent pacing faster than the programmed upper rate.
This is atrial sense to ventricular sense. The AV interval is shortened to 65 ms due to a prior atrial event within 500 ms. The AV interval is extended to prevent pacing faster than the upper rate.
This is atrial sense to ventricular sense in the AV (Sense) interval.
This is atrial sense to ventricular sense refractory in the AV (Sense) interval.
This is atrial sense to ventricular sense refractory in the shortened (65 ms) AV (Sense) interval. The AV interval was shortened due to a prior atrial event within 500 ms.
This is atrial pace to ventricular sense refractory in the AV (Pace) interval.
This is atrial pace to ventricular sense refractory.
This is atrial pace to ventricular sense after the Safety Pace window of 110 milliseconds.
This is atrial sense to ventricular pace at the AV (Sense) interval.
This is atrial sense to ventricular pace at the programmed upper rate interval.
The AV interval is extended to prevent pacing faster than the upper rate.
This is atrial pace to ventricular sense inside the Safety Pace window of 110 milliseconds. It will cause a ventricular pace at an A-V interval of 110 milliseconds.
This is atrial pace to ventricular sense inside the Safety Pace window but Safety Pacing is programmed OFF.
This is atrial sense to ventricular pace at the shortened AV interval of 65 ms.
The AV interval was shortened due to a prior atrial event within 500 ms.
This is atrial sense to ventricular pace with a shortened AV

TABLE 5-continued

EXPLANATORY TEXT interval of 65 ms.
The AV interval was shortened due to a prior atrial event within 500 ms. The V. pace time occurred at the programmed upper rate.
This is atrial pace to ventricular pace.
This is atrial pace to atrial sense refractory.
This is ventricular sense to atrial sense. No PVC has occurred.
This is ventricular sense to atrial sense. A PVC has occurred.
This is ventricular sense to atrial sense. The VA starts at the end of the AV interval, not at the V. sense, to preserve A-A timing. The A. sense will inhibit atrial pace.
This is ventricular sense to atrial pace occurring at the v-a escape time.
This is ventricular sense to atrial pace at the VA escape time. The VA interval starts at the end of the AV interval.
This is ventricular sense to atrial pace. A PVC has occurred, so the pvarp is extended to 400 ms.
This is ventricular sense to atrial pace. A PVC has occurred, so the pvarp is extended to 400 ms. The VA interval starts at the end of the AV interval to preserve A-A timing.
This is ventricular sense refractory to atrial pace, which occurs at the VA escape time.
This is ventricular sense refractory to atrial pace. A PVC has occurred, so the pvarp is extended to 400 ms.
This is ventricular sense to ventricular sense. A PVC has occurred, so the pvarp is extended to 400 ms.
This is ventricular sense to ventricular sense. A PVC has occurred, so the pvarp is extended to 400 ms. The VA interval starts at the end of the AV interval to preserve A-A timing.
This is ventricular sense to ventricular sense. A PVC has occurred, but the pvarp is programmed greater than or equal to 400 ms, so no extension is needed.
This is ventricular sense to ventricular sense. A PVC has occurred, but the pvarp is programmed greater dm or equal to 400 ms, so no extension is needed. The VA interval starts at the end of the AV.
This is ventricular sense to ventricular sense refractory.
The VA interval is not restarted by the refractory event.
This is ventricular sense to ventricular sense refractory.
The VA interval starts at the end of the AV interval, and is not restarted by the refractory event.
This is ventricular sense to ventricular sense refractory.
The VA interval is not restarted by the refractory event.
This is ventricular sense refractory to ventricular sense.
This is ventricular sense refractory to ventricular sense refractory.
This is ventricular sense or sense refractory to ventricular pace.
This is a Safety Pace event.
This is ventricular sense or sense refractory to ventricular pace.
This is a Safety Pace event, but the programmed A-V interval is less than 110 milliseconds.
This is ventricular sense to atrial sense refractory.
This is ventricular sense to atrial sense refractory. The VA interval starts at the end of the programmed AV interval.
This is ventricular sense to atrial sense refractory. A PVC has occurred, so the pvarp will be extended to 400 ms.
This is ventricular pace to atrial sense.
This is Safety Pace to atrial sense.
This is ventricular pace to atrial sense refractory.
This is Safety Pace to atrial sense refractory.
This is ventricular pace to atrial pace at the v-a escape time.
This is Safety Pace to atrial pace at the v-a escape time. The VA interval starts at the end of the programmed AV interval, not at the V. pace, in order to preserve A-A timing.
This is ventricular pace to ventricular sense.
This is Safety Pace to ventricular sense.
This is ventricular pace to ventricular sense refractory. This qualifies as a PVC because there is no intervening atrial event.
This is Safety Pace to ventricular sense refractory.
This is ventricular pace to ventricular sense refractory. This qualifies as a PVC because there is no intervening atrial event.
This is Safety Pace to ventricular sense refractory.
This is ventricular pace to ventricular sense refractory. This qualifies as a PVC because there is no intervening atrial event.
This is Safety Pace to ventricular sense refractory.
This is ventricular sense to sensor-driven atrial pace. The VA interval starts at the V. sense. The sensor-driven pace is recognized by the shortened VA interval and the different pace symbol.
This is ventricular sense to sensor-driven atrial pace. The VA interval starts at the V. sense. A PVC has occurred, so the pvarp is extended to 400 ms.
This is ventricular sense refractory to sensor-driven atrial pace. The sensor-driven pace is recognized by the shortened VA interval and the different pace symbol.
This is ventricular sense refractory to sensor-driven atrial pace. The sensor-driven pace is recognized by the shortened VA interval and the different pace symbol. A PVC-extended pvarp is present.
This is ventricular pace to sensor-driven atrial pace. The sensor driven pace is recognized by the shortened VA interval and the different pace symbol.
This is Safety Pace to sensor-driven atrial pace. The VA interval starts at the end of the programmed AV interval, not at the Safety Pace, to preserve A-A timing.
This is ventricular pace to atrial sense refractory caused by forced 8:7 block.
This is atrial sense refractory to atrial sense refractory in the AV (Sense) interval.
This is atrial sense refractory to atrial sense refractory, within the AV (Pace) interval.
This is atrial sense refractory to atrial sense refractory, within the AV (Sense) interval. The AV interval is extended to prevent pacing faster than the upper rate.
This is atrial sense refractory to atrial sense refractory, after an atrial sensed event. The AV interval has been extended to prevent pacing faster than the upper rate.
This is atrial sense refractory to atrial sense refractory. The first event is in pvarp; the second event is blocked from starting an AV interval due to forced 8:7 blocking.
This is atrial sense refractory in pvarp to atrial sense. Atrial pace is inhibited.
This is atrial sense refractory to ventricular sense within the AV (Sense) interval.
This is atrial sense refractory in AV to ventricular sense.
This is atrial sense refractory in AV to ventricular sense. The AV interval is extended to prevent pacing faster than the programmed upper rate.
This is atrial sense refractory in an automatically shortened AV to ventricular sense. The AV interval is extended to prevent pacing faster than the programmed upper rate.
This is atrial sense refractory in AV (Sense) to ventricular pace at the end of the AV interval.
This is atrial sense refractory in AV (Pace) to ventricular pace at the end of the AV interval.
This is atrial sense refractory to ventricular pace at the programmed upper rate. The AV interval was extended to prevent pacing faster than the upper rate.
This is atrial sense refractory in pvarp to atrial pace at the VA escape interval. An AV interval is started.
This is atrial sense refractory in a PVC-extended pvarp to atrial pace at the VA escape interval. An AV interval is started.
This is atrial sense refractory in pvarp to sensor-driven atrial pace.
This is atrial sense refractory in pvarp to sensor-driven atrial pace. A PVC has occurred, so the pvarp is extended to 400 ms.
This is atrial sense refractory in pvarp to ventricular sense. The VA interval is restarted.
This is atrial sense refractory in pvarp to ventricular sense refractory. The VA interval is not restarted.
This is ventricular sense refractory to atrial sense refractory in pvarp. The VA interval is not restarted.
This is ventricular sense refractory to atrial sense refractory in a PVC-extended pvarp. The VA interval is not restarted.
This is ventricular sense refractory to atrial sense refractory in an AV (Sense) interval.
This is ventricular sense refractory to atrial sense refractory in the AV interval. The AV has been extended to prevent pacing faster than the upper rate.
This is ventricular sense refractory to atrial sense refractory in the AV interval.
This is ventricular sense refractory to atrial sense. The VA interval is not restarted. Atrial pace is inhibited.

TABLE 5-continued

EXPLANATORY TEXT

This is ventricular sense refractory to atrial sense. A PVC
has occurred, so the pvarp is extended to 400 ms. The VA interval
is not restarted. Atrial pace is inhibited.
This is atrial sense refractory to atrial sense. The refractory
event was caused by forced 8:7 block.
This is atrial sense refractory to atrial pace at the VA escape
interval. The refractory event was caused by forced 8:7 block.
This is atrial sense refractory to ventricular sense. The
refractory event was caused by forced 8:7 block.
This is ending with atrial sense.
This is ending with atrial sense refractory.
This is ending with atrial pace.
This is ending with ventricular sense.
This is ending with ventricular sense refractory.
This is ending with ventricular pace.
This is the default ending condition.
This is an error condition.
This is a continuation condition.

The following Table 6 sets forth some examples of "hypertext" messages which may be linked to the explanatory messages of Table 5, as discussed hereinabove:

TABLE 6

The Diagnostic Disgrain looks for a known sequence of
markers before it starts to draw the timing.
Timing refers to the time intervals between Marker Channel
events produced by the pacemaker.
In adaptive rate pacing, the sensor can cause a pacing rate which
varies between the Lower Rate and the Upper Rate.
Lower Rate is the programmed minimum pacing rate.
Upper Rate is the programmed maxilinum pacing rate.

From the foregoing detailed description of a specific embodiment of the invention, it should be apparent that an implantable device system capable of providing an event marker diagram useable in an interactive fashion has been disclosed. Although a specific embodiment of the invention has been described herein in some detail, it is to be understood that this is solely done for the purpose of illustrating various features and aspects of the present invention and is not intended to be limiting with respect to the scope of the invention. It is contemplated that various substitutions, alterations, and/or modifications, including but not limited to those specifically discussed herein, may be made to the disclosed embodiment without departing from the spirit and scope of the invention as defined in the appended claims.

For example, it has been noted herein that the manner in which a user selects an area of the Marker Channel™ Diagram, so that a context-sensitive explanatory textbox appears on the display, can vary from implementation to implementation. A stylus, light-pen, touch screen, mouse, or cursor control keypad are each considered viable alternatives, and others may be available. Similarly, it has been noted that there are numerous commercially-available software-based expert system packages available, and it is believed that those of ordinary skill in the art having the benefit of this disclosure will be capable of practicing the present invention using any or all of these; alternatively, a customized expert system may be prepared.

What is claimed is:

1. A medical device system, comprising:
    an implantable device including a pulse generator having means for generating stimulating pulses and sensor circuitry means for detecting physiological events;
    implantable device control circuitry coupled to said pulse generator and to said sensing circuitry, said control circuitry operative to trigger said pulse generator to deliver said stimulating pulses in response to physiological events;
    a transmitter circuit coupled to said implantable device control circuitry further comprising telemetry circuitry responsive to delivery of said stimulating pulses and detection of said physiological events by said sensor circuitry means for transmitting event marker signals;
    an external unit having a graphics display screen, said external unit further comprising:
    a receiver circuit means for receiving said event marker signals and means for displaying sequences of said event marker signals on said graphics display screen;
    means for storing a knowledge base comprising information concerning operational characteristics of said implantable device;
    a user input device having means for enabling a user to select a point within a displayed sequence of said event marker signals on said graphics display screen;
    means responsive to selection of a point within a displayed sequence of event marker signals for applying the information in said knowledge base to the sequence of event marker Signals to generate an explanatory message explaining operation of said implantable device at said selected point; and
    means for displaying said explanatory message on said graphics display screen.

2. A system in accordance with claim 1, wherein said user input device is a mouse.

3. A system in accordance with claim 1, wherein said physiological events include ventricular and atrial depolarizations.

4. A system in accordance with claim 1, wherein said implantable device comprises an implantable pacemaker/cardioverter/defibrillator.

5. A system according to claim 1 wherein said means for selecting comprises means for selecting a point between displayed event marker signals.

6. A system according to claim 1 wherein said means for selecting comprises means for selecting a displayed event marker signal.

7. A system according to claim 1 wherein said implantable device is capable of operating in a plurality of operational modes and wherein said knowledge base comprises information concerning each of said operational modes.

8. A method of operating an implantable medical device system comprising the steps of:
    (a) storing a knowledge base comprising information concerning operational characteristics of an implantable device in an external unit having a display screen;
    (b) transmitting, from said implantable device, a sequence of event marker signals reflecting occurrences of at least one predetermined type of operation of said implantable device;
    (c) receiving said sequence of transmitted event marker signals in said external unit;
    (d) displaying, on said display screen, a diagrammatic representation of said sequence of event marker signals;
    (e) selecting a point on said display screen lying within said displayed sequence of event marker signals;
    (f) responsive to selection of said point on said display screen, analyzing said sequence of event marker signals using said knowledge base to generate an explanatory message explaining operation of said implantable device at said selected point; and (g) displaying, on said display screen, said explanatory message.

9. A method in accordance with claim 8, wherein said at least one predetermined type of physiologic event includes atrial and ventricular depolarizations, and wherein a unique event marker is transmitted for each type of physiologic event.

10. A method in accordance with claim 8, wherein said at least one predetermined type of operation of said implantable device includes delivery of stimulation pulses by said implantable device.

* * * * *

UNITED STATES PATENT AND TRADEMARK OFFICE
CERTIFICATE OF CORRECTION

PATENT NO. : 5,549,654

DATED : Aug. 27, 1996

INVENTOR(S) : Richard M. Powell

It is certified that error appears in the above-identified patent and that said Letters Patent is hereby corrected as shown below:

| | |
|---|---|
| C. 2  L. 9 | "state-of-the art" to be changed to "state-of-the-art" |
| C. 6  L. 26 | "an in" to be changed to "and in" |
| C. 12 L. 10 | "may provided" to be changed to "may be provided" |
| C. 12 L. 47 | "plurality patient" to be changed to "plurality of patient" |
| C. 15 L. 10 | "regions" to be changed to "region" |
| C. 15 L. 61 | "will be displayed" to be changed to "to be displayed" |
| C. 16 L. 21 | "select an suitable" to be changed to "select a suitable" |

UNITED STATES PATENT AND TRADEMARK OFFICE
CERTIFICATE OF CORRECTION

PATENT NO. : 5,549,654

DATED : Aug. 27, 1996

INVENTOR(S) : Richard M. Powell

It is certified that error appears in the above-identified patent and that said Letters Patent is hereby corrected as shown below:

*C. 18 L. 56-59* "This is atrial sense to ventricular pace at the programmed upper rate interval.
The AV interval is extended to prevent pacing faster than the upper rate."
*to be changed to* "This is atrial sense to ventricular pace at the programmed upper rate interval. The AV interval is extended to prevent pacing faster than the upper rate."

*C. 18 L. 62-65* "This is atrial sense to ventricular pace at the shortened AV interval of 65 ms.
The AV interval was shortened due to a prior atrial event within 500 ms."
*to be changed to* "This is atrial sense to ventricular pace at the shortened AV interval of 65 ms. The AV interval was shortened due to a prior atrial event within 500 ms."

*C. 18 L. 67 - C. 19 L. 5-7* "This is atrial sense to ventricular pace with a shortened AV interval of 65 ms.
The AV interval was shortened due to a prior atrial event within 500 MS. The V. pace time occured at the programmed upper rate."
*to be changed to* "This is atrial sense to ventricular pace with a shortened AV interval of 65 ms. The AV interval was shortened due to a prior atrial event within 500 MS. The V. pace time occured at the programmed upper rate."

*C.19 L. 34, 35* "This is ventricular sense to ventricular sense refractory.
The VA interval is not restarted by the refractory event."
*to be changed to* "This is ventricular sense to ventricular sense refractory. The VA interval is not restricted by the refractory event."

*C. 19 L. 36-38* "This is ventricular sense to ventricular sense refractory.
The VA interval starts at the end of the AV interval, and is not restarted by the refractory event."
*to be changed to* "This is ventricular sense to ventricular sense refractory. The VA interval starts at the end of the AV interval, and is not restarted by the refractory event."

*C. 19 L. 38, 39* "This is ventricular sense to ventricular sense refractory.
The VA interval is not restarted by the refractory event."
*to be changed to* "This is ventricular sense to ventricular sense refractory. The VA interval is not restarted by the refractory event."

UNITED STATES PATENT AND TRADEMARK OFFICE
CERTIFICATE OF CORRECTION

PATENT NO. : 5,549,654
DATED : August 27, 1996
INVENTOR(S) : Richard M. Powell

It is certified that error appears in the above-identified patent and that said Letters Patent is hereby corrected as shown below:

C. 22 L. 23    "Signals" to be changed to "signals"
C. 13 L. 33    "Channel" to be changed to "Channel"
C. 17 L. 5    "(msec)" to be changed to "(mSec)"
C. 19 L. 33    "greater dm or equal" to be changed to "greater than or equal"
C. 21 L. 26    "Disgrain" to be changed to "Diagram"
C 21 L. 32    "maxilinum" to be changed to "maximum"

Signed and Sealed this

Seventh Day of December, 1999

Attest:

Q. TODD DICKINSON

*Attesting Officer*     *Acting Commissioner of Patents and Trademarks*